(12) United States Patent
Hong et al.

(10) Patent No.: US 11,850,441 B2
(45) Date of Patent: Dec. 26, 2023

(54) ADJUSTABLE FOCUS MAGNETIC STIMULATION COIL

(71) Applicants: University of Maryland, Baltimore, Baltimore, MD (US); University of Maryland, Baltimore County, Baltimore, MD (US)

(72) Inventors: L. Elliot Hong, Ellicott City, MD (US); Fow-Sen Choa, Ellicott City, MD (US); Qinglei Meng, Catonsville, MD (US)

(73) Assignees: University of Maryland, Baltimore, Baltimore, MD (US); University of Maryland, Baltimore County, Baltimore, MD (US)

(*) Notice: Subject to any disclaimer, the term of this patent is extended or adjusted under 35 U.S.C. 154(b) by 52 days.

(21) Appl. No.: 16/739,650

(22) Filed: Jan. 10, 2020

(65) Prior Publication Data

US 2020/0222709 A1  Jul. 16, 2020

Related U.S. Application Data

(60) Provisional application No. 62/791,060, filed on Jan. 11, 2019.

(51) Int. Cl.
| | |
|---|---|
| *A61N 2/02* | (2006.01) |
| *H01F 7/20* | (2006.01) |
| *H01F 27/28* | (2006.01) |
| *A61N 2/00* | (2006.01) |
| *H01F 27/255* | (2006.01) |

(52) U.S. Cl.
CPC ............ *A61N 2/02* (2013.01); *A61N 2/004* (2013.01); *H01F 7/20* (2013.01); *H01F 27/255* (2013.01); *H01F 27/28* (2013.01)

(58) Field of Classification Search
CPC .......... H01F 1/066; H01F 29/08; H01F 29/12; H01F 7/14; H01F 7/17; A61N 2/00; A61N 2/004; A61N 2/006; A61N 2/008; A61N 2/02
See application file for complete search history.

(56) References Cited

U.S. PATENT DOCUMENTS

| | | | | | |
|---|---|---|---|---|---|
| 933,767 | A | * | 9/1909 | Lasher ............... | H01F 29/12 336/41 |
| 1,469,213 | A | * | 10/1923 | Douglass ............ | H01F 29/12 336/124 |

(Continued)

FOREIGN PATENT DOCUMENTS

WO    WO 2015199151    * 12/2015    ............. B60L 53/12

*Primary Examiner* — Carrie R Dorna
(74) *Attorney, Agent, or Firm* — Whiteford, Taylor & Preston, LLP; Gregory M. Stone

(57) ABSTRACT

Disclosed is an electromagnetic coil system for use during transcranial or transdermal stimulation procedures, in which an electrically conductive coil wraps around a magnetic core at an oblique wrapping angle to provide a more directed focal spot size at a given depth inside of, for example, a patient's body. In certain configurations, the electrically conductive coil may be adjustable with respect to the magnetic core, such that the wrapping angle of the electrically conductive coil may be modified to, in turn, adjust the focal spot size of the induced electric field generated by the system as may desired to concentrate the field at a particularly desired location.

5 Claims, 9 Drawing Sheets

(56) References Cited

U.S. PATENT DOCUMENTS

| | | | | |
|---|---|---|---|---|
| 1,709,786 A | * | 4/1929 | Gibbs | H01F 29/12 |
| | | | | 336/41 |
| 1,753,337 A | * | 4/1930 | Given | H01F 21/005 |
| | | | | 336/79 |
| 2004/0263307 A1 | * | 12/2004 | Christopherson | H01F 21/04 |
| | | | | 336/174 |
| 2019/0255346 A1 | * | 8/2019 | Ghiron | A61N 2/006 |

* cited by examiner

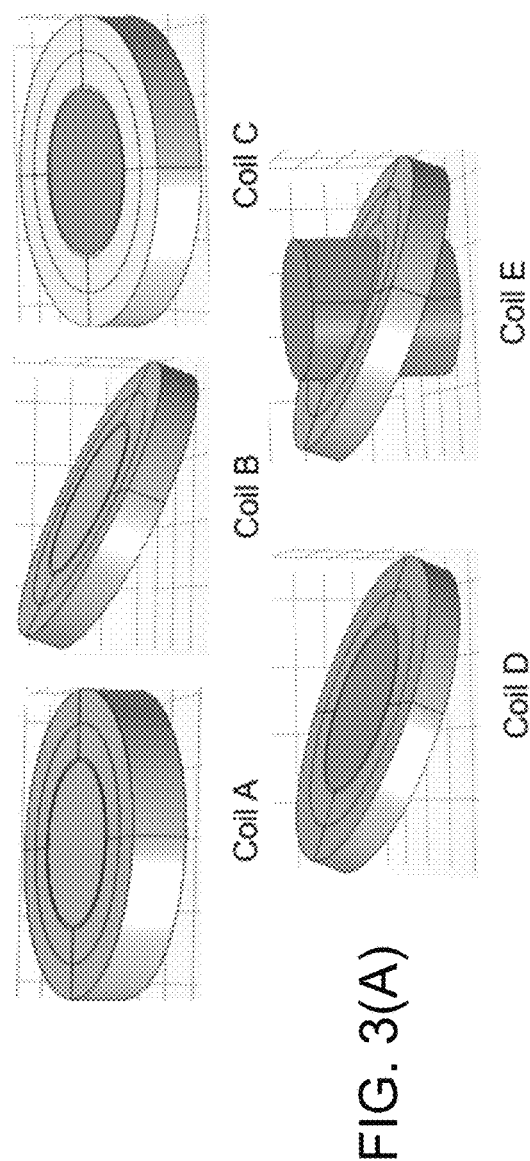
FIG. 3(A)
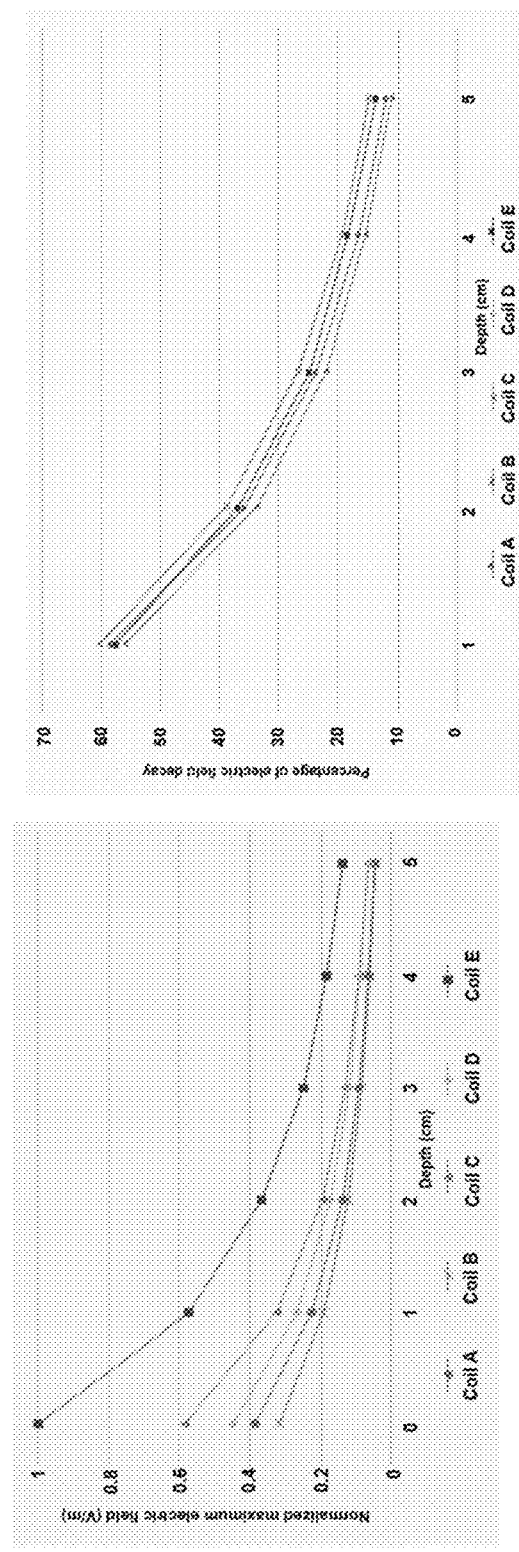
FIG. 3(B)
FIG. 3(C)

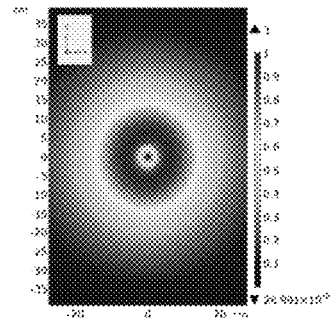
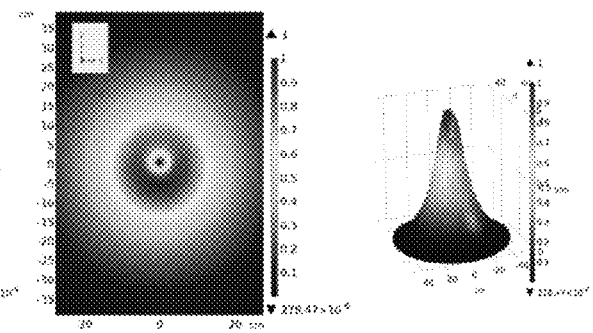
FIG. 4(A)
FIG. 4(B)
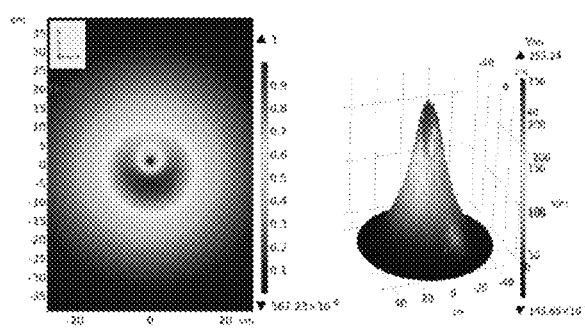
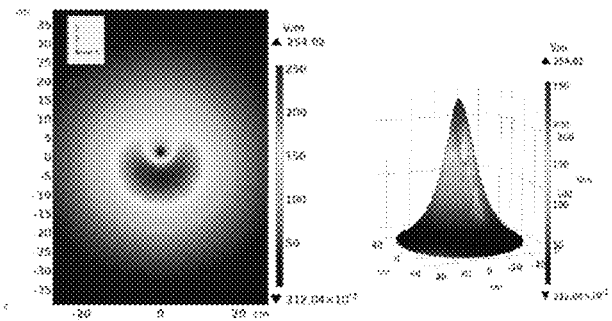
FIG. 4(C)
FIG. 4(D)
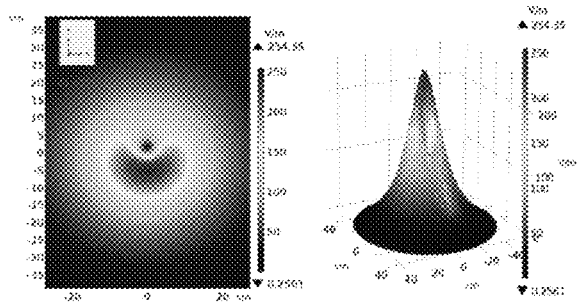
FIG. 4(E)

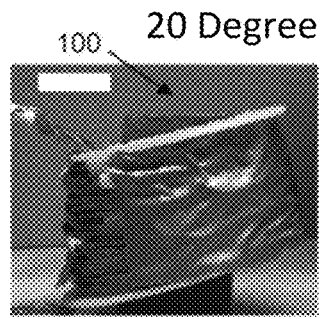 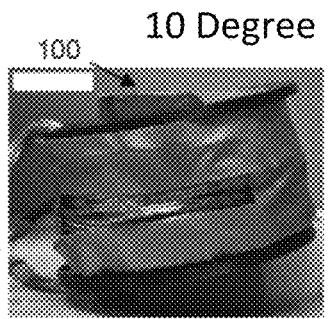 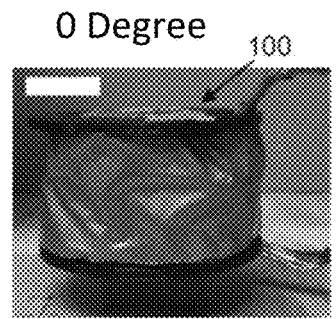
FIG. 10(A)  FIG. 10(B)  FIG. 10(C)
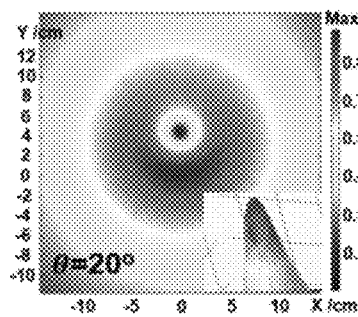 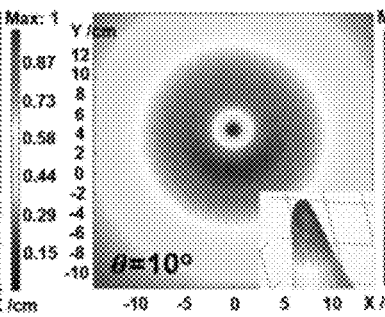 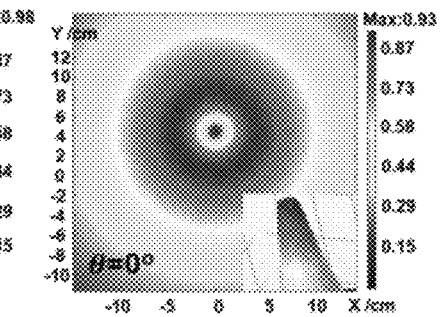
FIG. 11(A)  FIG. 11(B)  FIG. 11(C)
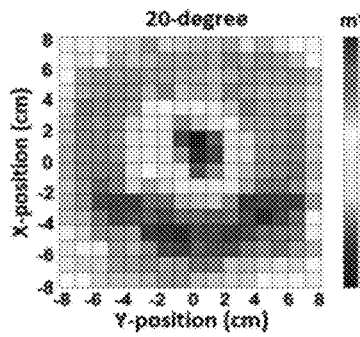 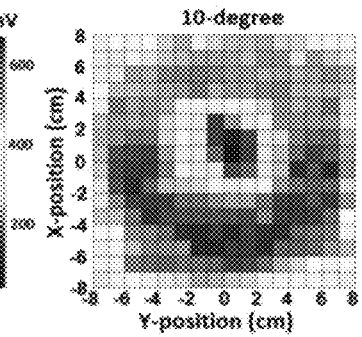 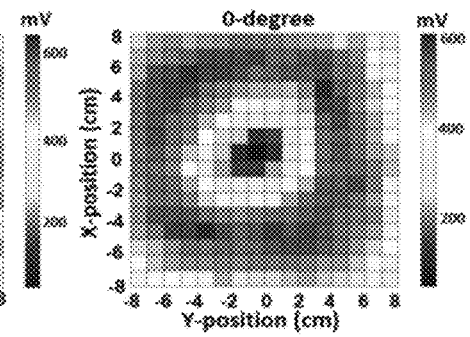
FIG. 12(A)  FIG. 12(B)  FIG. 12(C)

ADJUSTABLE FOCUS MAGNETIC STIMULATION COIL

CROSS REFERENCE TO RELATED APPLICATION

This application claims the benefit of U.S. Provisional Application No. 62/791,060 titled "Adjustable Focus TMS Coil," filed Jan. 11, 2019 by the inventors herein, which application is incorporated herein by reference in its entirety.

STATEMENT OF GOVERNMENT SUPPORT

This invention was made with government support under Grant No. 1631820 awarded by the National Science Foundation. The Government has certain rights in the invention.

FIELD OF THE INVENTION

The present invention relates generally to devices for the generation of magnetic fields, and more particularly to a device for generating a magnetic field including an electromagnetic coil system, such as for use in transcranial or transdermal magnetic stimulation, in which the focal spot size of the magnetic field may be adjustable through angling of an electrically conductive coil.

BACKGROUND

Deep brain stimulation ("DBS") has been employed for treatment of a variety of neurological and neurodegenerative diseases. However, despite the promise offered by DBS systems and methods, it is an invasive procedure that requires brain surgery through the skull and insertion of electrodes into deep brain regions. Such surgery risks damaging existing functional brain cells, and is often performed only as a last resort.

Transcranial magnetic stimulation ("TMS"), on the other hand, is a non-invasive brain stimulation method that uses transient pulse field induced currents to cause neuronal depolarization and hyperpolarization in brain cortices. It induces a small electrical current, which stimulates nerve cells including their branches and allows for the study of brain functions and the development of new treatments for brain disorders. Currently available coil designs struggle with the inability to stimulate the brain in a focused region and at the tissue depths necessary to treat the foregoing diseases and disorders.

Unfortunately, for previously known TMS systems, there is rapid attenuation in depth of the electric field with such conventional stimulation coils, resulting in a depth-focality tradeoff. More particularly, a magnetic field spreads and becomes less focused as it penetrates an object, such as deep brain regions. The generated magnetic field often is generally too weak (i.e., produces a weak electrical field) to electrically activate tissues beyond 2 cm away from the stimulator. As a result, brain stimulation by transcranial magnetic stimulation tools is mainly limited to cortical surface areas, even though many neuropsychiatric disorders are initiated from deeper brain regions.

In light of the foregoing limitations, there is a need for devices that may provide increased focus of a magnetic field at greater depths than previously available magnetic stimulation systems.

SUMMARY OF THE INVENTION

Disclosed herein is an electromagnetic coil system for use during transcranial or transdermal stimulation procedures, in which an electrically conductive coil wraps around a magnetic core at a wrapping angle that is between 0° and 90°, and more preferably between 0° and 40°, resulting in a magnetic stimulation system having a smaller focal spot size at a given depth inside of, for example, a patient's body than previously known magnetic stimulation systems. For example, the focal spot size at a fixed depth can be a covered area in which field intensity is greater than 50% of the peak field intensity at this fixed depth. In certain configurations, the electrically conductive coil may be movably mounted with respect to the magnetic core or the direction of magnetic stimulation, such that the wrapping angle of the electrically conductive coil may be modified to, in turn, adjust the focal spot size of the magnetic field generated by the system as may desired to concentrate the field at a particularly desired location. In other configurations, sets of magnetic coils may be provided in varying configurations that enable their mounting on the magnetic coil at differing angles to alter the focal spot size of the magnetic field generated by the system.

In accordance with certain features of an embodiment of the invention, an electromagnetic coil system is provided comprising: a magnetic core having a longitudinal axis along a length of the magnetic core; and an electrically conductive coil wrapped around the magnetic core at a wrapping angle that is oblique to the longitudinal axis of the magnetic core.

In accordance with further features of an embodiment of the invention, an electromagnetic coil system is provided comprising: a magnetic core having a longitudinal axis along a length of the magnetic core; and an electrically conductive coil movably mounted on the magnetic core to vary a wrapping angle of the coil around the magnetic core to an angle that is oblique to the longitudinal axis of the magnetic core.

In accordance with still further features of an embodiment, a method for applying magnetic stimulation is provided, comprising: providing an electromagnetic coil system comprising a magnetic core having a longitudinal axis along a length of the magnetic core, and an electrically conductive coil wrapped around the magnetic core at a wrapping angle that is oblique to the longitudinal axis of the magnetic core; and modifying the wrapping angle to modify a stimulation focal spot size of a magnetic field generated by the electromagnetic coil system.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized. The present invention is illustrated by way of example, and not by way of limitation, in the figures of the accompanying drawings, in which like reference numerals refer to similar elements, and in which:

FIG. 3(A) is a perspective view of varying configurations of magnetic stimulation coils, all of equal dimensions.

FIG. 3(B) is a graph of field strength as a function of depth for the magnetic stimulation coils shown in FIG. 3(A).

FIG. 3(C) is a graph of normalized field decay rate as a function of depth for the magnetic stimulation coils shown in FIG. 3(A).

FIG. 4(A) is a graphical representation of an electric field strength of a magnetic stimulation coil having a wire wrapping angle of 0°.

FIG. 4(B) is a graphical representation of an electric field strength of a magnetic stimulation coil having a wire wrapping angle of 10°.

FIG. 4(C) is a graphical representation of an electric field strength of a magnetic stimulation coil having a wire wrapping angle of 20°.

FIG. 4(D) is a graphical representation of an electric field strength of a magnetic stimulation coil having a wire wrapping angle of 30°.

FIG. 4(E) is a graphical representation of an electric field strength of a magnetic stimulation coil having a wire wrapping angle of 40°.

FIGS. 10(A)-10(C) show fabricated electromagnetic coil systems having angled wire wrapping at 20°, 10°, and 0°, respectively.

FIGS. 11(A)-11(C) show COMSOL simulations of the generated electric field distributions of the coils of FIGS. 10(A)-10(C), respectively, at a depth of 2 cm away from the coils.

FIGS. 12(A)-12(C) show the measured electric field distributions of the coils of FIGS. 10(A)-10(C), respectively, at a depth of 2 cm away from the coils.

DETAILED DESCRIPTION OF THE PREFERRED EMBODIMENTS

The following detailed description is provided to gain a comprehensive understanding of the methods, apparatuses and/or systems described herein. Various changes, modifications, and equivalents of the systems, apparatuses and/or methods described herein will suggest themselves to those of ordinary skill in the art.

Descriptions of well-known functions and structures are omitted to enhance clarity and conciseness. The terminology used herein is for the purpose of describing particular embodiments only and is not intended to be limiting of the present disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced items.

The use of the terms "first", "second", and the like does not imply any particular order, but they are included to identify individual elements. Moreover, the use of the terms first, second, etc. does not denote any order of importance, but rather the terms first, second, etc. are used to distinguish one element from another. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Although some features may be described with respect to individual exemplary embodiments, aspects need not be limited thereto such that features from one or more exemplary embodiments may be combinable with other features from one or more exemplary embodiments.

Figure 1:
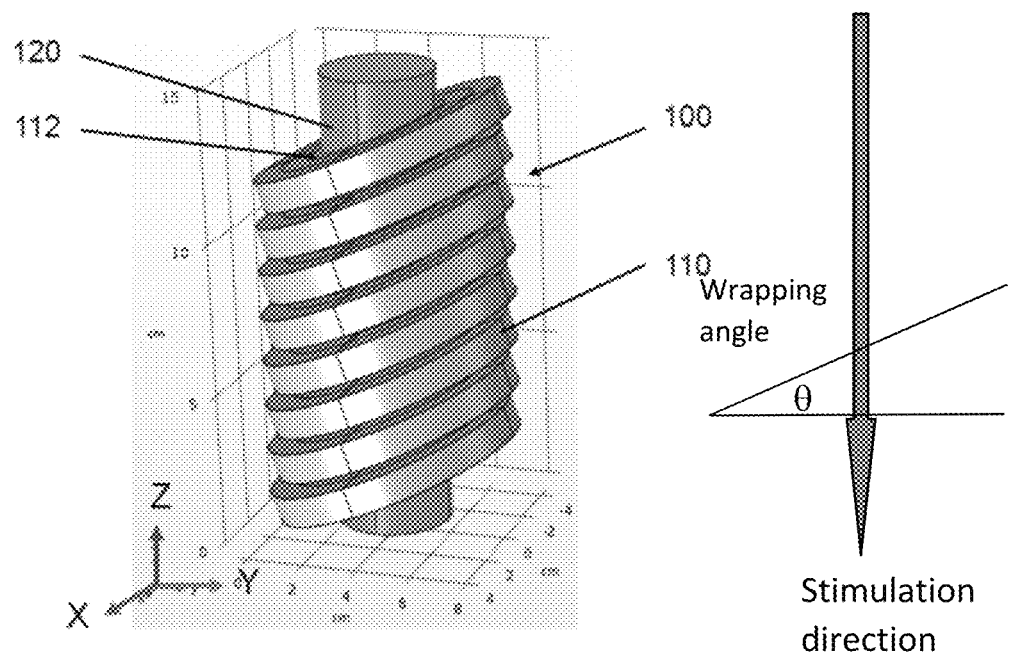
FIG. 1 is a perspective view of an electromagnetic coil system in accordance with certain aspects of an embodiment of the invention.
Figure 2:
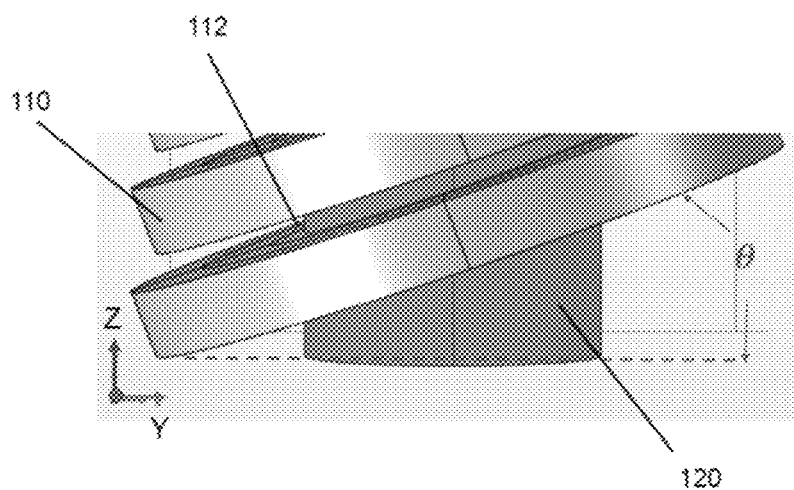
FIG. 2 is a close-up side view of a portion of the electromagnetic coil system of FIG. 1.

With reference to FIGS. 1 and 2, an electromagnetic coil system 100 in accordance with certain aspects of an embodiment of the invention may be provided for transcranial or transdermal magnetic stimulation ("TMS"), in which electromagnetic radiation is used to stimulate or affect activity in a field and at a depth in a subject. By way of non-limiting example, such an electromagnetic coil system 100 may form one or more of the combined magnetic core and coil elements in a system for controlling magnetic fields and magnetic field induced currents as described in U.S. Pat. No. 10,518,098 of Hong et al., and U.S. Patent Application Pub. No. 2018/0193658 of Hong et al., the specifications of which are incorporated herein by reference in their entireties.

The electromagnetic coil system 100 of FIGS. 1 and 2 may, in certain configurations, be adjustable such that an electric field focality (in two-dimensions and in three-dimensions) may have a variable size, and the depth of the magnetic field generated by the system may have a variable distance. More particularly, the angle θ at which an electrically conductive coil 110 wraps around a magnetic core 120 of the electromagnetic coil system 100 (i.e., a "wrapping angle" of electrically conductive coil 110 about magnetic core 120) may be modified between 0° and an angle less than 90°, and more preferably between 0° and 40°, with such modification of the wrapping angle resulting in a change in at least the size of the electric field focality, and preferably the depth of the magnetic field. The electromagnetic coil system 100 is configured to generate an asymmetric field such that it is capable of having a sufficient value at larger depths within a patient's brain compared to typical TMS devices, and of having sufficient focality or focal spot size (i.e., a sufficiently small focal spot size compared to typical TMS devices), to affect the intended physiological response within the subject. Further, the focal spot size may be adjustable to provide for use in a variety of differing applications, such as for variously sized patients, stimuli locations, mammals, etc.

With continuing reference to the exemplary embodiment of FIGS. 1 and 2, electromagnetic coil system 100 includes magnetic core 120 and electrically conductive coil 110, which together are configured to effectively collect magnetic field and keep the magnetic field diffuse along a magnetic core direction (e.g., generally parallel to a longitudinal axis of the magnetic core 120). By wrapping the wires of electrically conductive coil 110 at a wrapping angle θ relative to the magnetic core direction, the symmetry of electrically conductive coil 110 is broken (i.e., is asymmetric with respect to the magnetic core direction). This asymmetry causes a concentration of, or focuses, the electric field and causes stimulations at lower power outputs compared to typical TMS devices. In certain configurations, the preferred wrapping angle is between 0° and 40°, and more preferably between 20° and 40°, although in other configurations the wrapping angle may be outside of this range, as further detailed below. For example, the magnetic field output along the magnetic core direction (e.g., due to the magnetic core, equivalent field emission aperture, and corresponding field divergent solid angles) are generally lower than typical TMS devices for similar levels of stimulation. Thus, the induced electric field has a smaller focal spot size and a similar field depth decay rate, and the depth-focality tradeoff exhibited by electromagnetic coil system 100 is improved in comparison to that of typical TMS devices.

In certain configurations, electromagnetic coil system 100 may be configured to have many or variable focal spot sizes. More particularly, the focal spot size may be adjusted by changing the wrapping angle, which as discussed above causes a concentration of the magnetic field. Thus, the electromagnetic coil system 100 may provide a variable stimulation focal spot size. In certain configurations in which the electrically conductive coil 110 of electromagnetic coil system 100 has a larger diameter (e.g., 24 cm), the magnetic field may have a field divergence angle that is smaller than typical (e.g., ~48°), such that the magnetic field may penetrate into deeper brain regions with a lower decay rate than typical TMS devices of similar diameters and voltage. Thus, the electromagnetic coil system 100 may be configured to adjust the focal spot size at least by adjusting the wire-wrapping tilted angle θ, while substantially maintaining a slow decay rate of field strength into brain deep regions.

Those skilled in the art will recognize that electrically conductive coil 110 may be mounted with respect to magnetic core 120 so as to enable modification of the wrapping angle in a wide variety of ways, including (by way of non-limiting example) a simple bracket that may movably hold the electrically conductive coil with respect to magnetic core 120 with, for instance, a hinged portion allowing one part of the bracket to move with respect to another part of the bracket, thus modifying the wrapping angle of the electrically conductive coil.

Alternatively, the interior wall 112 of electrically conductive coil 110 may be pitched at an angle so as to only allow its positioning about magnetic core 120 at a specific wrapping angle, with multiple sets of electrically conductive coils 110 having varying pitches being provided to each achieve a desired wrapping angle of between 0° and 40°, and more preferably between 20° and 40°. Other configurations for pivotably mounting electrically conductive coil 110 with respect to magnetic core 120 will readily occur to those of ordinary skill in the art, and do not depart from the spirit and scope of the instant invention.

In certain configurations, magnetic core 120 may comprise an iron core. However, magnetic core 120 may alternatively be formed of other materials, including by way of non-limiting example nickel, cobalt, iron oxide, composite and powder magnetic materials, air, and the like. As shown in FIGS. 3(A)-3(C), providing electrically conductive coil 110 with a positive wrapping angle θ improves (compared to typical TMS devices) stimulation by producing a peak electric field at particular depths. FIG. 3(A) illustrates five varying TMS coil configurations implemented in COMSOL (finite element analysis software, readily commercially available from COMSOL, Inc.). All of the coils shown in FIG. 3(A) share the same dimensions and ampere turns; specifically, the inner and outer diameters are 5 cm and 9 cm, respectively, and the coil thickness is 1 cm. All of the coils shown in FIG. 3(A) were driven with the same ampere-turns at 1 MHz. Coil A comprises a typical ring shape air-core coil device with a flat (zero-degree) wire wrapping angle. Coil B comprises a ring shape air-core coil with 20° wrapping angle. Equivalently, coil B is a 20° wrapping angle coil A. Coil C comprises an iron core ring coil with a flat wire wrapping angle. Coil D is equivalent to a Coil C with a 20° wrapping angle. Finally, Coil E is similar in configuration to Coil D, but the magnetic core of Coil D is straight (i.e., not tilted or angled with the electrically conductive coil), and the magnetic core has a length that extends to align with the edges of the tilted electrically conductive coil. Induced electric field distributions generated by each of the coils shown in FIG. 3(A) by each coil were then calculated by COMSOL at different depth levels (within X-Y planes with a variable of Z coordinate) and the decay rates were compared.

FIGS. 3(B) and 3(C) compare the normalized electric field strength and field decay rate at different depths for each of the coil configurations shown in FIG. 3(A). At a wrapping angle of 20°, Coil B delivered relatively lower field strength at each of the depths analyzed in comparison to Coil A. The decay percentage rates of Coil B at each depth level are nearly the same as Coil A. Comparing Coil C with Coil A, a magnetic core inserted into the coil center helps to enhance field strength by around 1.4 to 1.5 times when the depth is around 1 cm. Coil D delivers a lower magnetic field than that of Coil C. A coil configured in accordance with certain aspects of an embodiment of the invention, as shown in Coil E, has significantly improved field strength at all depths compared with Coil C. FIG. 3(B) shows the normalized field decay rate as a function of depth and all five types of coils from FIG. 3(A) share a similar depth decay rate. As indicated from FIGS. 3(B) and 3(C), Coil E (configured in accordance with certain aspects of an embodiment of the invention) has similar depth decay rate compared to other coils, but significantly improves field focusing and enhances field strength.

An electromagnetic coil system in accordance with certain aspects of an embodiment may be configured to adjust the focal spot size, for example, to become very small, compared to typical TMS devices. However, the depth-dependent electric field strength decay rate is not substantially affected by the change of the focal spot size. FIGS. 1 and 2 show an electromagnetic coil system employing an electrically conductive coil 110 with a high number of turns (e.g., 100 turns). However, electrically conductive coil 110 may have a lower number of turns, such as 90 turns, 80 turns, 70 turns, or the like. In addition, electrically conductive coil 110 may have a higher number of turns, such as 200 turns, 300 turns, etc. Electrically conductive coil 110 preferably has inner and outer diameters that are approximately 5 cm and 9 cm, respectively. For the examples evaluated herein, the length of magnetic cores 120 was kept at 15 cm as a constant. However, other inner and outer diameters are feasible, depending on the application of the coil device.

Figure 5:
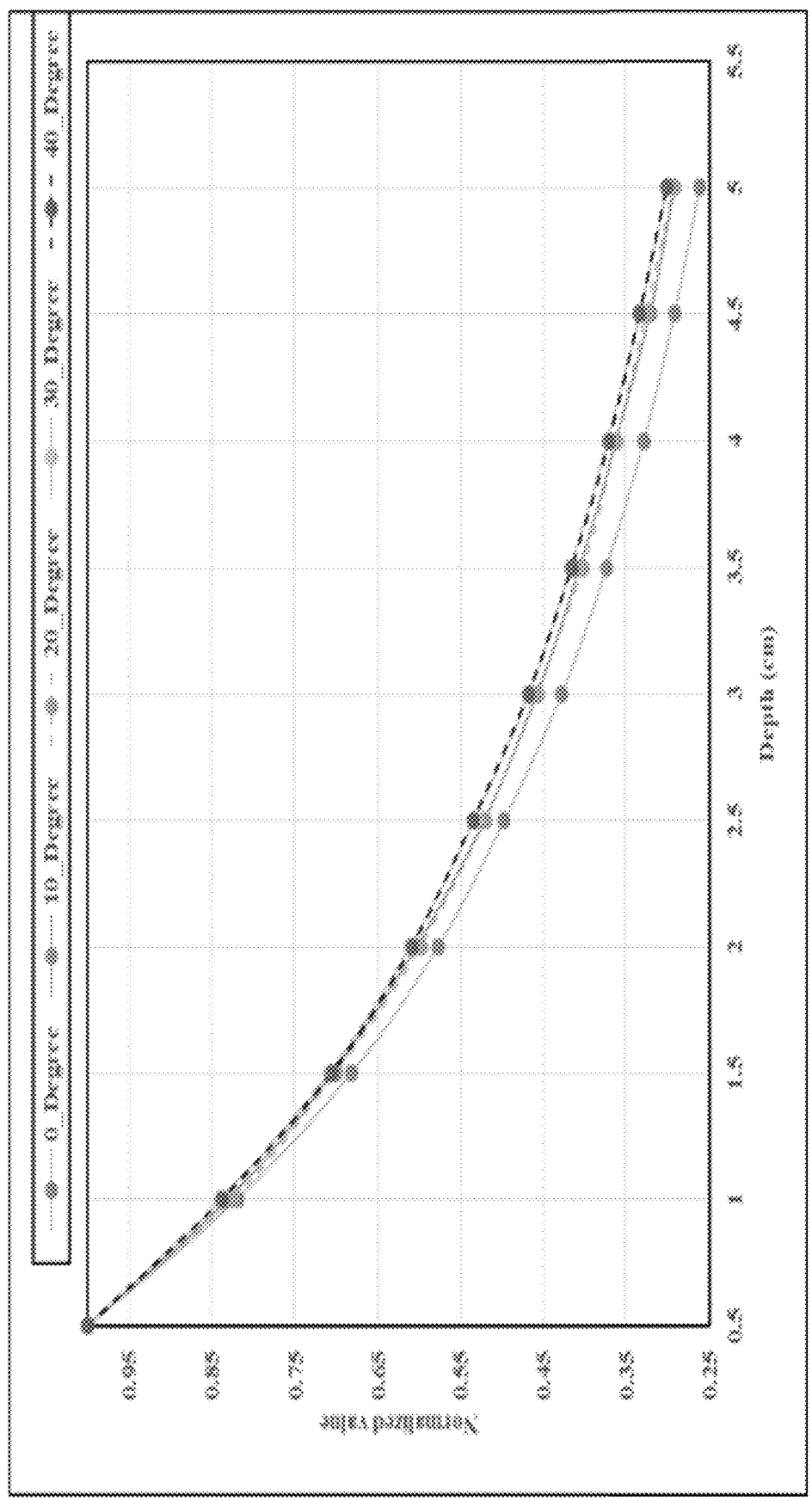
FIG. 5 is a graph depicting normalized depth decay rates of magnetic stimulation coils having wrapping angles from 0° to 40°.
Figure 6:
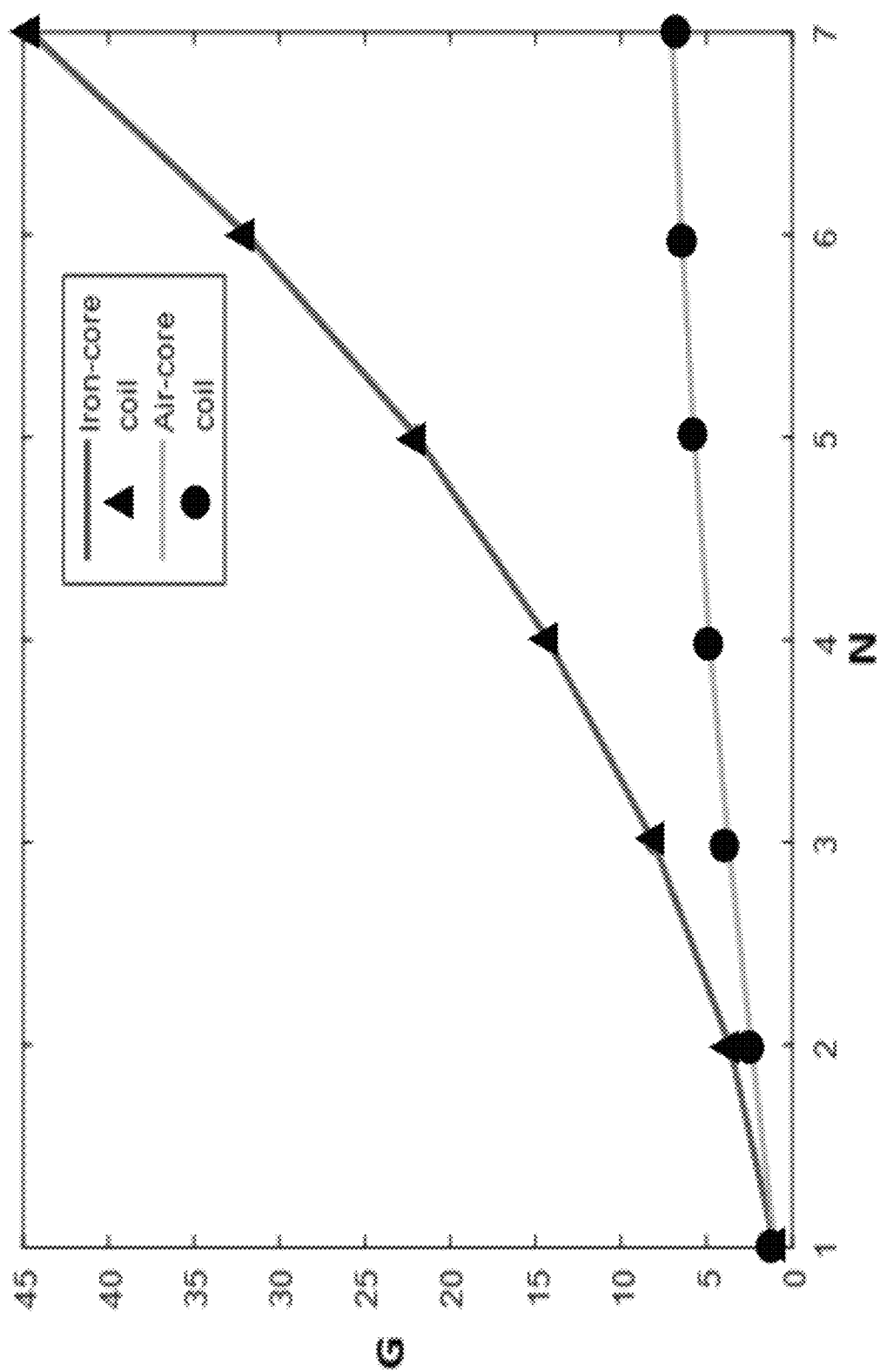
FIG. 6 is a graph depicting electric field strength build-up as a function of coil turns in an electromagnetic coil system according to certain aspects of an embodiment of the invention.

When the wire wrapping angle is changed from, for example, between 0, 10, 20, 30, and 40 degrees, the 2-D and 3-D expressions of the electric field distribution, which is 2 cm away from the coil, are shown in FIGS. 4(A), 4(B), 4(C), 4(D), and 4(E), respectively. The induced field is more focused when the wrapping angle of the coil device is larger. The tip point of the electric field can be very sharp when the angle is larger than 30 degrees. FIG. 5 shows the normalized electric field strength decay percentage rates (0-100%) of the five coils depicted in FIGS. 4(A)-4(E), which normalized to the highest field strength when measured at a location close to the coil. As shown in FIG. 5, the decay rate stays nearly the same for all of these coils. FIG. 6 shows the induced electric field strength by coil devices having magnetic cores of air and iron when the number of wiring turns is increased. Electromagnetic coil systems 100 having magnetic cores 120 made of iron generally have faster and super-linear field strength growth rates, compared to magnetic cores of air, because the electrically conductive coil 110 can more effectively collect the magnetic field when the length of the electromagnetic coil system 100 is increased.

Figure 7:
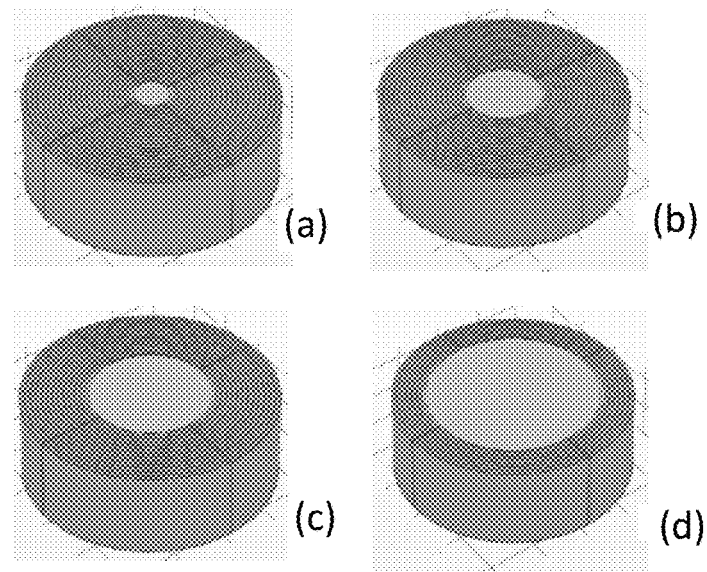
FIG. 7 is a perspective view of electromagnetic coil systems having diameters of approximately 24 cm with iron magnetic core sizes of (a) 3.5 cm, (b) 7.5 cm, (c) 11.5 cm, and (d) 15.5 cm.
Figure 8:
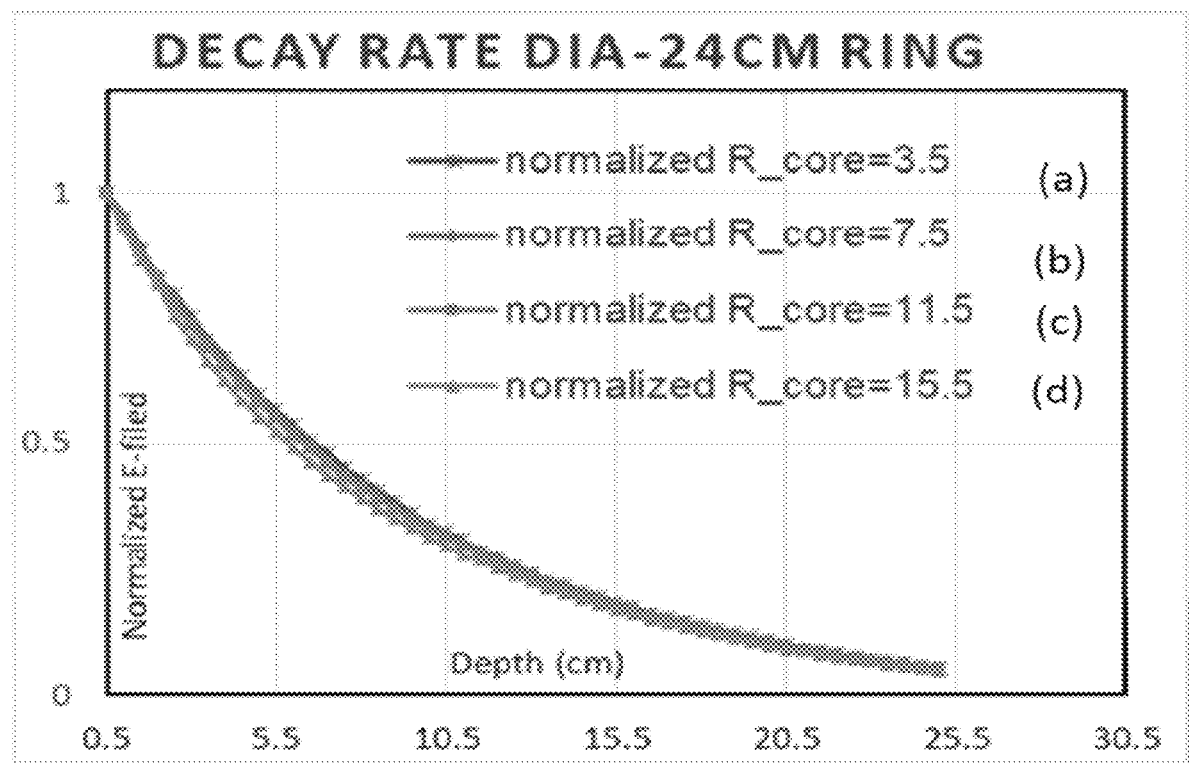
FIG. 8 is a graph depicting normalized electric field strength decay rates with depth of the electromagnetic coil systems depicted in FIG. 7.
Figure 9A:
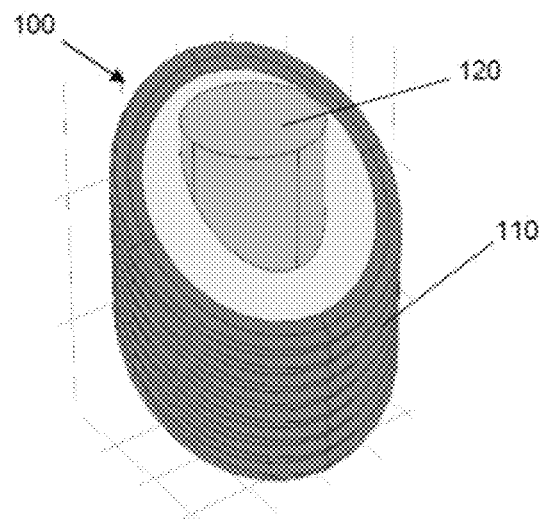
FIG. 9(A) is a perspective view of a large (e.g., 17 cm) diameter electromagnetic coil system with a 40° wire wrapping angle in accordance with certain aspects of an embodiment of the invention.
Figure 9B:
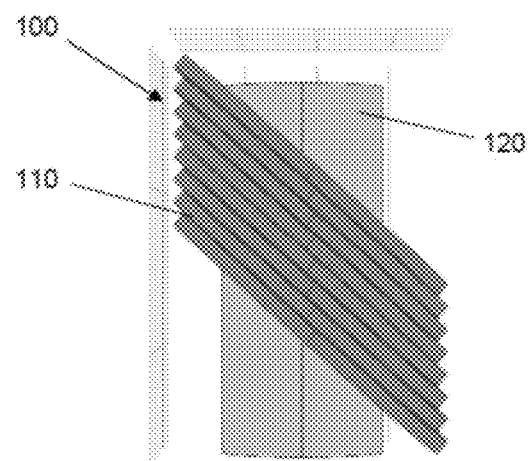
FIG. 9(B) is a side view of the electromagnetic coil system of FIG. 9(A).
Figure 9C:
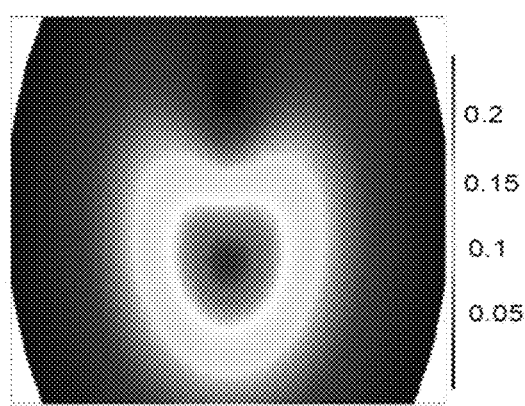
FIG. 9(C) is 2-D plot of the distribution of the electrical field generated by the electromagnetic coil system of FIGS. 9(A) and 9(B) at 5 cm (depth) away from the coil.
Figure 9D:
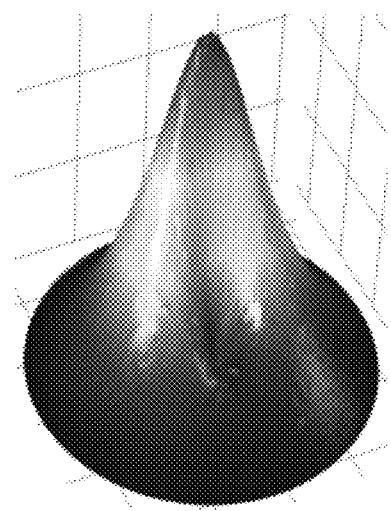
FIG. 9(D) is 2-D plot of the distribution of the electrical field generated by the electromagnetic coil system of FIGS. 9(A) and 9(B) at 5 cm (depth) away from the coil.

As discussed above, electromagnetic coil systems 100 having larger diameters and larger apertures (compared to smaller diameters and apertures) can generate a more compact (i.e., less spreading) magnetic field distribution. FIG. 7 shows electromagnetic coil systems each having diameters of approximately 24 cm (a)-(d) with different iron core sizes. Their normalized depth decay rate is shown in FIG. 8, where all 4 different coil systems have approximately the same depth decay rate. All of the coil systems can penetrate depths greater than 5.5 cm while maintaining more than half of their respective field strengths. Thus, some embodiments may include multiple electromagnetic coil systems 100 (e.g., three electromagnetic coil systems) operating in parallel such that the total magnetic and electric field vectors at, e.g., 5 cm depth, are summed so that the focal spot can have an increased field strength in comparison to (e.g., approximately between 1 and 1.5 times greater than) the highest field strength that can be induced by typical individual TMS coil devices at the model surface near each individual stimulator output. In embodiments having angled wire wrapping, as described above, the generated field can be further focused and enhanced to accomplish even higher strength.

FIGS. 9(A)-9(D) show an exemplary electromagnetic coil system 100 according to certain aspects of an embodiment of the invention, having a diameter of 17 cm with 40° angled wire wrapping. The generated electric field distribution, 5 cm away from the coil, is color- and 3-D represented at FIGS. 9(C) and 9(D). The magnetic field is generally highly focused in the transverse plane, but the focal spot size can gradually expand along the longitudinal axis. Such an electromagnetic coil system 100 may be used, for example, to stimulate brain regions deeper than cortical areas. Further, in certain configurations, multiple or arrays of electromagnetic coil systems 100 may be configured to prevent regions above the region of interest from also being stimulated.

In an exemplary configuration, electromagnetic coil systems 100 having magnetic cores 120 formed of silicon steel plates were used to experimentally verify simulation-predicted results. The electromagnetic coil systems 100 included wire holders with different wrapping angles of approximately 0°, 10°, and 20°. The wire holders may be formed using typical manufacturing methods, such as machining, additive manufacturing, injection molding, and the like. The electromagnetic coil systems 100 were provided the same length and inner and outer diameters, which were 5 cm, 9 cm and 15 cm, respectively. Each electrically conductive coil was wrapped 64 turns litz wires, which contain a bundle of 135 pieces of 30 gauge wires in parallel. FIGS. 10(A), 10(B) and 10(C) show 3 coils with 20°, 10°, and 0° wire wrapping angles, respectively.

Figure 13:
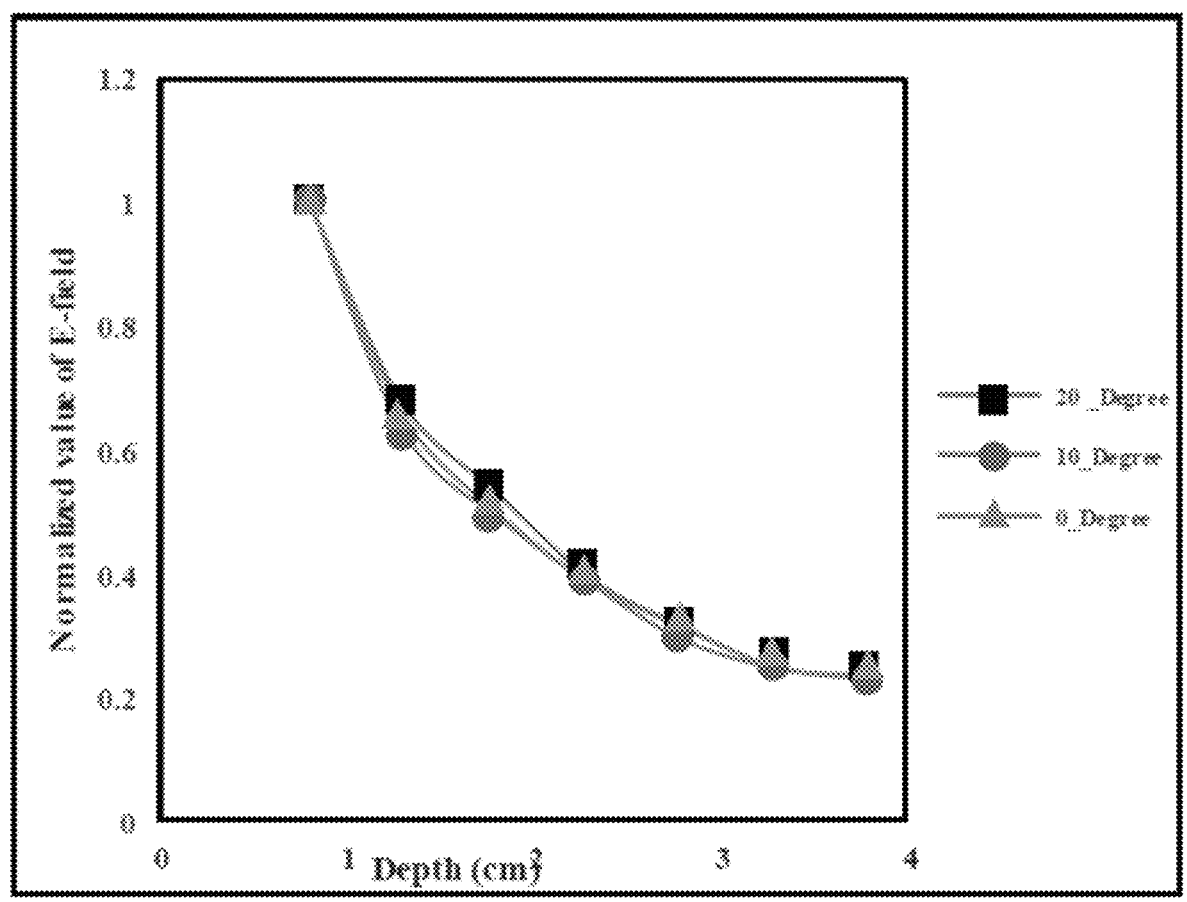
FIG. 13 is a graph depicting the measured electric field strength of the 20°, 10°, and 0° coils of FIGS. 10(A)-10(C) at different depths away from the coils.

With one power supply, a capacitor bank was set to 100V and pulse duration was 250 µs. Using a Magstim power supply, the power percentage was set to approximately 5%. The induced electric field was measured by a modified Rogowski probe at a depth of 2 cm away from the coils. Because the electric field components along the Z-axis (direction of magnetic core axis) was generally small enough to be negligible, only field components on the X and Y axes were measured. Measurements were taken for every 1 mm step within the X-Y plane, and an area of 16 cm by 16 cm was scanned for each coil. The measured field distribution result in FIGS. 12(A)-12(C) match well with the predicted field distributions shown in FIGS. 11(A)-11(C). Furthermore, both theoretical and experimental results demonstrate that the larger the tilted wrapping angle, the higher the peak field strengths of a coil device having angled wires, with the same current load. FIG. 13 shows the measured depth dependence of the field strengths of the 3 electromagnetic coil systems of FIGS. 10(A)-10(C), normalized to each coil device's peak electric field strength. They share nearly the same decay rates, which verified theoretical prediction. Thus, an electromagnetic coil system configured in accordance with the foregoing description may provide an adjustable focal spot size without substantially degrading depth performance.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. Thus, it should be understood, therefore, that the invention may be practiced otherwise than as specifically set forth herein.

What is claimed is:

1. A method for applying transcranial or transdermal magnetic stimulation, comprising:
   providing an electromagnetic coil system comprising:
      a magnetic core having a longitudinal axis along a length of the magnetic core; and
      an electrically conductive coil wrapped around the magnetic core at a wrapping angle that is oblique to the longitudinal axis of the magnetic core, wherein said electronically conductive coil is pivotably mounted directly on said magnetic core to pivot about an axis that is perpendicular to the longitudinal axis of the magnetic core to modify a stimulation focal spot size of a magnetic field generated by said electromagnetic coil system upon a change of said wrapping angle;
   positioning said electromagnetic coil system adjacent a portion of a patient's body that is to receive the magnetic stimulation; and
   modifying said wrapping angle to modify the stimulation focal spot size of the magnetic field inside of said patient's body that is generated by said electromagnetic coil system.

2. The electromagnetic coil system of claim 1, wherein said wrapping angle is adjustable to between 0°, at which said electromagnetic coil encircles a circumference of said core, and 40° from a line that is perpendicular to the longitudinal axis of the magnetic core.

3. The electromagnetic coil system of claim 1, wherein said wrapping angle is adjustable to between 20° and 40° from a line that is perpendicular to the longitudinal axis of the magnetic core.

4. The electromagnetic coil system of claim 1, wherein said magnetic core further comprises an iron core.

5. The electromagnetic coil system of claim 1, wherein said magnetic core further comprises one or more of iron, iron oxide, nickel, cobalt, composite magnetic materials, powder magnetic materials, and air.

* * * * *